US006695768B1

(12) United States Patent
Levine et al.

(10) Patent No.: US 6,695,768 B1
(45) Date of Patent: Feb. 24, 2004

(54) ADJUSTABLE PERIVENTRICULAR RING/RING LIKE DEVICE/METHOD FOR CONTROL OF ISCHEMIC MITRAL REGURGITATION AND CONGESTIVE HEART DISEASE

(76) Inventors: Robert A. Levine, c/o Jules Levine, 465 West End Ave., 12-A, New York, NY (US) 10024; Nadia Nathan, 11 Maguire Rd., Wayland, MA (US) 01778; Mark Handschumacher, c/o Massachusetts General Hospital, Cardiac Ultrasound, VBK 523, 55 Fruit St., Boston, MA (US) 02114; J. Luis Guerrero, 40 Cross St., Norton, MA (US) 02766

( * ) Notice: Subject to any disclaimer, the term of this patent is extended or adjusted under 35 U.S.C. 154(b) by 0 days.

(21) Appl. No.: 09/538,328

(22) Filed: Mar. 29, 2000

Related U.S. Application Data

(60) Provisional application No. 60/126,933, filed on Jul. 15, 1999, provisional application No. 60/126,814, filed on Mar. 30, 1999, and provisional application No. 60/127,240, filed on Jun. 18, 1999.

(51) Int. Cl.[7] .................... A61F 2/00; A61F 13/00

(52) U.S. Cl. .................... 600/37

(58) Field of Search .................... 600/37, 18; 607/129; 606/174, 205

(56) References Cited

U.S. PATENT DOCUMENTS

| | | | |
|---|---|---|---|
| 5,501,698 A * | 3/1996 | Roth et al. | 606/174 |
| 6,077,218 A * | 6/2000 | Alferness | 600/37 |
| 6,123,662 A * | 9/2000 | Alferness et al. | 600/37 |
| 6,183,411 B1 | 2/2001 | Mortier et al. | 600/16 |
| 6,190,408 B1 | 2/2001 | Melvin | 623/3.1 |
| 6,221,103 B1 | 4/2001 | Melvin | 623/3.1 |
| 6,332,893 B1 | 12/2001 | Mortier et al. | 623/2.36 |
| 6,402,679 B1 | 6/2002 | Mortier et al. | 600/16 |
| 6,406,420 B1 | 6/2002 | McCarthy et al. | 600/16 |
| 6,409,760 B1 | 6/2002 | Melvin | 623/3.1 |

* cited by examiner

*Primary Examiner*—Max F. Hindenburg
*Assistant Examiner*—Brian Szmal
(74) *Attorney, Agent, or Firm*—Perkins, Smith & Cohen; Jerry Cohen; John A. Hamilton

(57) ABSTRACT

This device aims at correcting distortions in spatial geometry and function of the heart muscle, thereby restoring valvular integrity and optimizing myocardial performance. The device is applied externally to the heart, fixed in the chest cavity or wall, while maintaining flexibility and selectively targeting specific points of varying size, tension, and force requirements. This minimally invasive device and method of application will contribute toward a reduced rate of mortality and morbidity from heart disease.

17 Claims, 8 Drawing Sheets

1
13
19
17
5
31
31
15

ADJUSTABLE PERIVENTRICULAR RING/ RING LIKE DEVICE/METHOD FOR CONTROL OF ISCHEMIC MITRAL REGURGITATION AND CONGESTIVE HEART DISEASE

CROSS REFERENCE TO RELATED APPLICATIONS

The present application claims the priority of provisional application Ser. Nos. 60/126,933 filed Jul. 15, 1999; 60/126, 814 filed Mar. 30, 1999 and 60/127,240 filed Jun. 18, 1999.

BACKGROUND OF THE INVENTION

This invention relates generally to the correction of valvular dysfunction and the localized reorientation of the structural and functional integrity of the distorted ventricular geometry, and, more particularly, to develop an adjustable periventricular ring/ring-like device for control of ischemic mitral regurgitation, and congestive heart disease and the method thereof.

Patients with ischemic heart disease have a wide range of pathological changes. Some of these include ventricular dilatation, dilatation of the mitral annulus, papillary muscle displacement and tethering, choral and papillary infarcts, segmental and global ventricular dysfunction. The mitral valve function and competency rests on the fine geometric and functional integrity of its supporting structures.

When the left ventricle dilates, the papillary muscles are tethered, thus preventing adequate closure of the mitral valve. The left ventricle has two papillary muscles. Both originate from the left ventricular free wall. The anterior papillary muscle is attached to the anterior wall of the left ventricle, close to its lateral border. The posterior papillary muscle originates from the posterior wall, near the junction of the interventricular septum. The mitral valve closure is effected by the apposition of its leaflets. Papillary muscle tethering has been shown to be one of the important mechanisms resulting in mitral valve incompetency, and failure of leaflet apposition.

There is controversy about the role of the myocardial contractility in the preservation of the valve competency. Loss of contractility and dilation of the mitral annulus might also play an important function. In summary, the spatial orientation affects the distribution of the tension effecting leaflet closure.

Previous work that addressed ischemic mitral regurgitation includes:

(a) Revascularization alone (Coronary Artery Bypass Grafting):

Czer et al. documented that revascularization alone does not improve mitral regurgitation. In a study of 2000 patients who underwent coronary artery bypass surgery, uncorrected mitral regurgitation nearly doubled the risk of late death.

(b) Annuloplasty:

Mitral valve annuloplasty addresses the mechanism pf annular dilation as a cause of ischemic mitral regurgitation. It could compensate for papillary muscle tethering to some extent, and improve mitral leaflet coaptation. However, clinical observations suggest that it does not correct for the actual tethering of the leaflets. In additon, annuloplasty techniques involve opening the heart which is more of an invasive approach than the suggested device.

(c) Pericardial restraint independently has been suggested to limit LV size.

(d) Surgical techniques developed by Batiste and Affiori have advocated resection of areas of the ventricle and surgically stitching the valve leaflets together, yet again an invasive procedure.

Other ventricular remodeling techniques and patents have been introduced, such as the acorn device which encircles the heart in global LV dilatation and does not address specific segmental pathology. The acorn device is not directed or fixed with out specifications. It does not provide selectivity of the target points nor adaptability. The fixation and tension are different from our device. Intraoperative observations suggest that force or pressure applied outside papillary muscle could eliminate the mitral regurgitation.

Another device, the myocor, includes a tensor member mechanism that is inserted inside the heart and changes the diameter of the ventricle at that point. This is more invasive than our device. The point of fixation is on the heart versus the sturdier rib cage in our invention.

Surgical methods utilizing alternating deflating balloons around the heart do not provide the precise localized augmentation of function that is required. These methods do not have precise targeting or sturdy fixation. Precise targeting and correction of the stress strain and displacement interactions are specifically important for the intricate geometry of the mitral valve.

Most if not all of these procudures, techniques, or devices have targeted a circumferential change in LV geometry versus a specific regional change in displacement, tension, and force.

It is therefore the object of the present invention to treat mitral regurgitation by directly addressing the disease of the ventricle and supporting structures as the underlying mechanism for the incompetency of the mitral valve in ischemic heart disease or any form of venticular geometric distortion.

It is another object of the present invention to treat segmental dysfunction and optimize global LV efficiency by optimizing the stress, strain displacement interactions. In essence, it could function as a ventricular assist device.

It is another object of the present invention to stabilize the beating heart for other operations when the pressure heads are set on negative suction.

It is a further object of the present invention to apply it on the right ventricle.

SUMMARY OF THE INVENTION

The objects set forth,, above as well as further and other objects and advantages of the present invention, are achieved by the embodiments of the invention described hereinbelow.

The present invention related to a device, which could deliver the targeted localized force, tension and displacement changes with a minimally invasive approach. It would prevent inordinate tension placed on the mitral valve or the relative stenosis that could occur with annuloplasty techniques.

The present invention relates more particularly to the restoration of mitra valve competency and compensates for the regional ventricular dysfunction in general and strain induced by papillary muscle tethering. It corrects for the displacement and forces on leaflet closure. An advantage of the localized force and displacement change, a feature of this device, is to avoid coronary flow impedance, minimize damage, and maximize impact.

One feature of the present invention is its stability around the heart, diverting fixation tension, leverage and stress from the heart to the rib cage; therefore delivering force or tension required to the specific point.

For a better understanding of the present invention, together with other and further objects thereof, reference is made to the accompanying drawings and detailed description and its scope will be pointed out in the appended claims.

DETAILED DESCRIPTION OF THE PREFERRED EMBODIMENTS

Figure 1A:
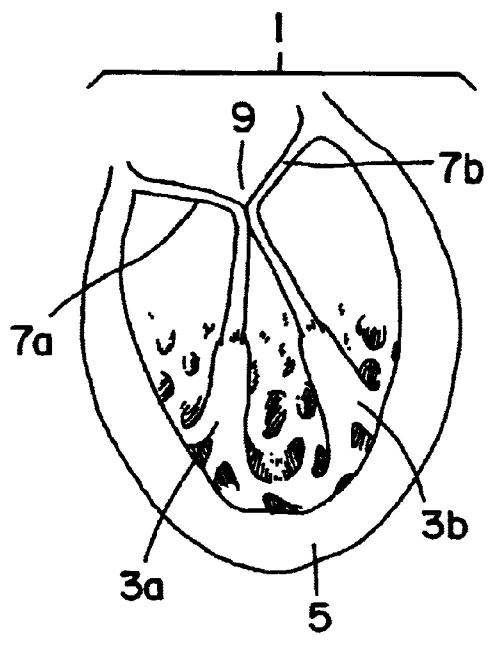
FIG. 1 shows tethering of papillary muscles.

Referring now to FIG. 1A, a cross-section of the left ventricle of a human heart 1 is shown. Papillary muscles 3*a* and 3*b* are shown extending from the ventricular free wall 5.

Figure 1B:
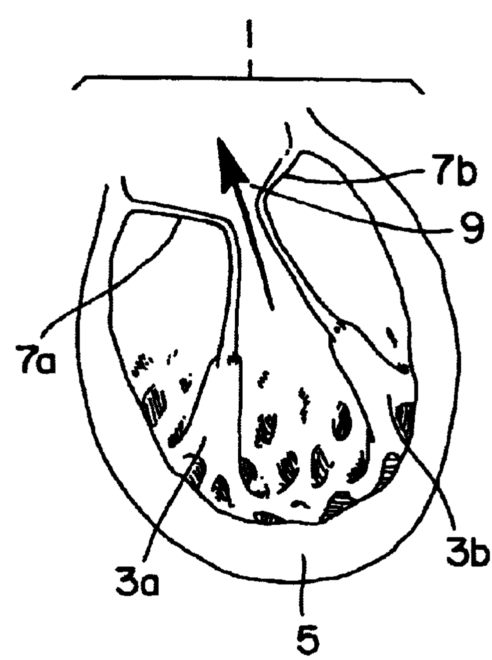

Leaflets 7*a* and 7*b* of the respective papillary muscles 3*a* and 3*b* comprise the mitral valve 9 and are shown in a fully closed position. FIG. 1B shows the same cross-sectional view of a diseased human heart 1 wherein the papillary muscles 3*a* and 3*b* are tethered resulting in a failure of the leaflets 7*a* and 7*b* to properly close the mitral valve 9 and thereby allowing mitral regurgitation to occur.

Figure 2:
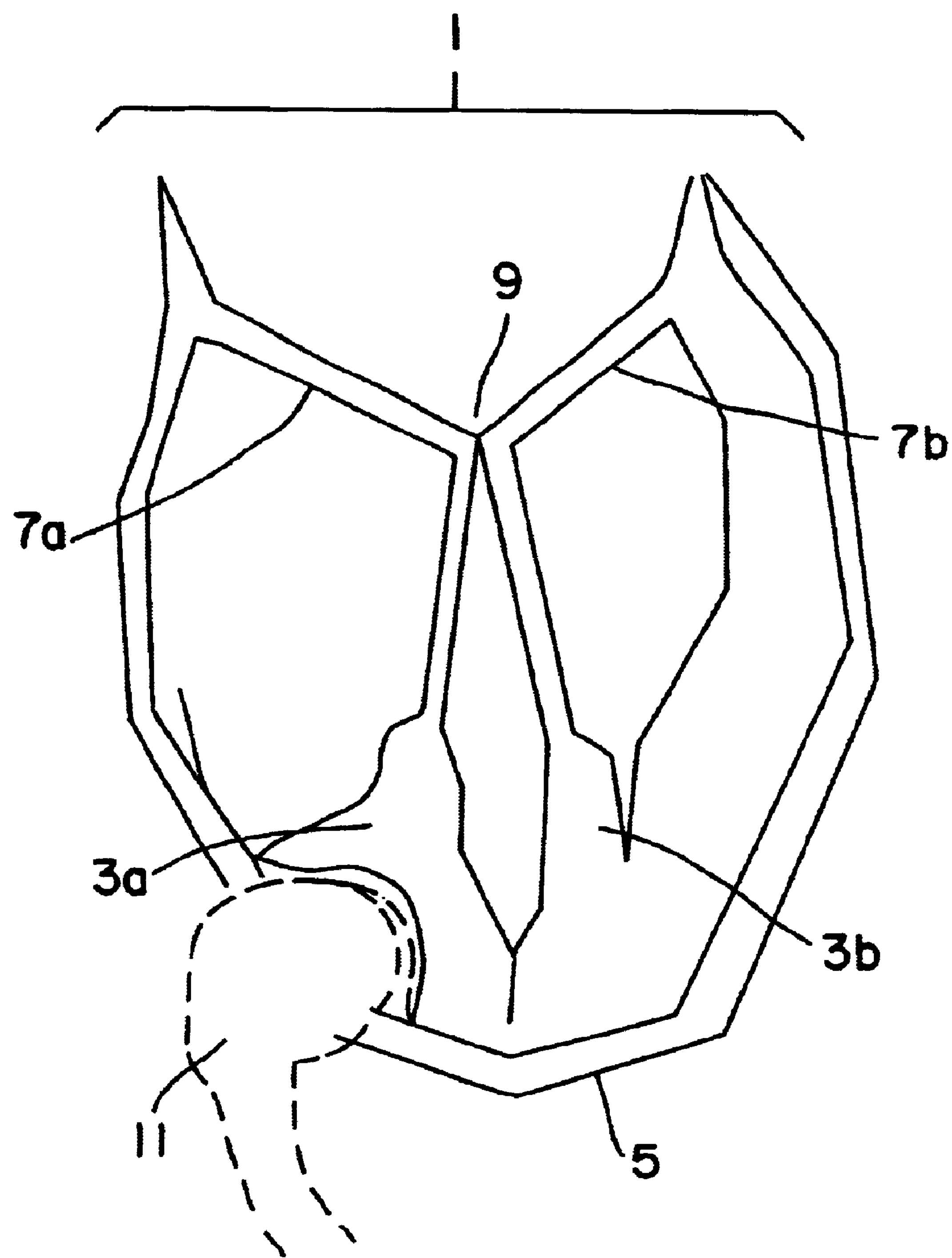
FIG. 2 shows how the device will correct tethering.

Now turning to FIG. 2, a cross-section of a ventricle of a human heart 1 is also shown wherein the present invention 11 is shown affixed to the ventricular free wall 5 such that papillary muscle 3*a* and its corresponding leaflet 7*a* is pushed upward to allow leaflet 7*a* to meet with leaflet 7*b* and fully close the mitral valve 9.

Figure 3:
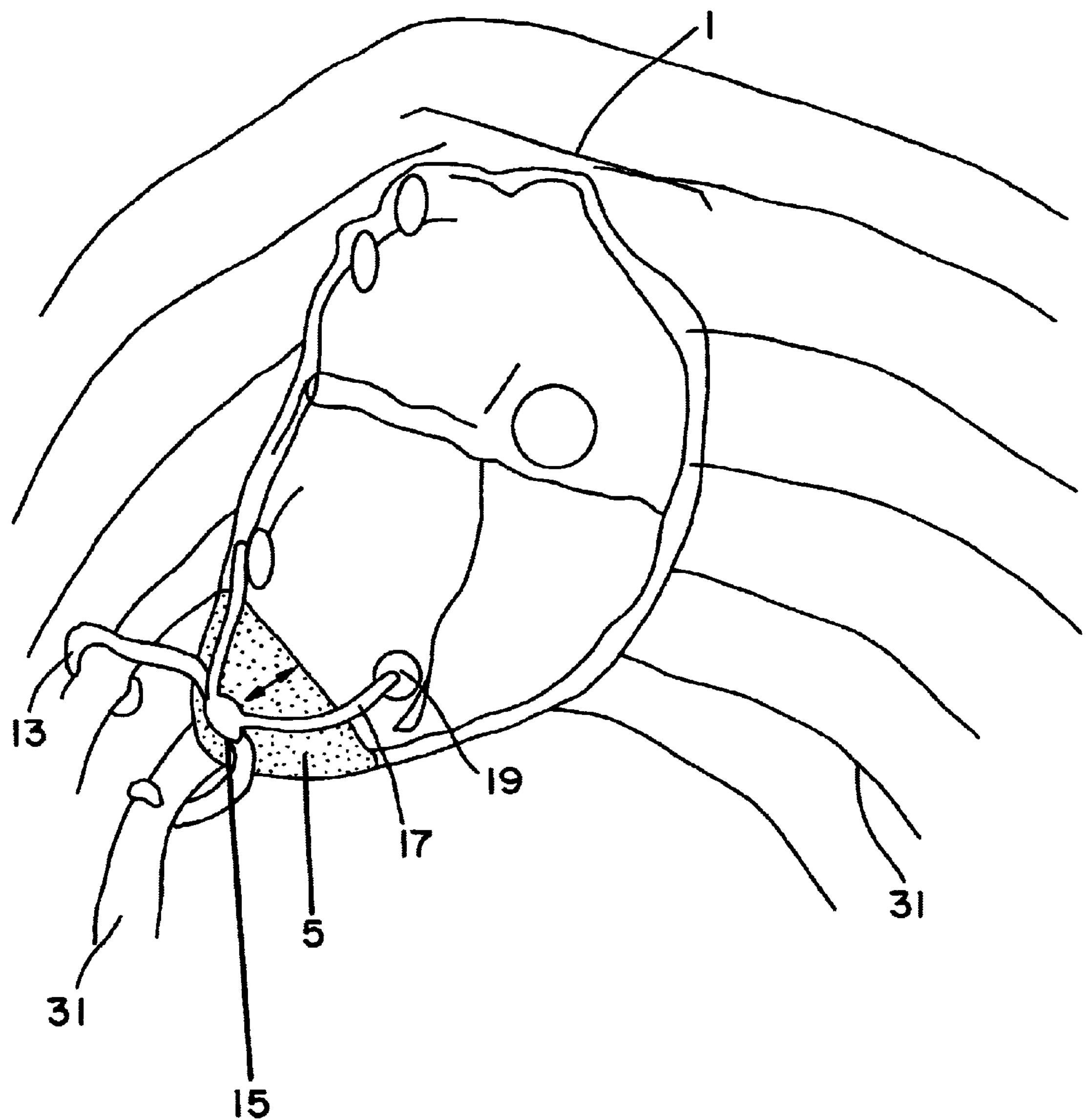
FIG. 3 shows components of the device and their application to the heart.

In FIG. 3, another view of the present invention is shown wherein the components of the present device include a supporting means 13, such as legs or brackets; a center part 15 on which rests swiveling adjustable arched arms 17 that hold pressure heads 19 at their ends. All components of this device are adjustable and adaptable to different surfaces, curvatures, and geometric orientations. The supporting means 13 may be provided by the light duty bracket. In our preferred embodiment, these brackets 13 would be angled and segmented, and would house spring-like tubing benders to avoid kinking. The joints of the brackets could be flexible overlapping, half lap comer, angled, or any other variation of such in different embodiments. Flexible angling coupling may join the different components of this device.

In the embodiment shown in FIG. 3, the center part 15 of the arms is a simple base fulcrum point, a base from which the arms 17 of the device extend to surround the heart 1 at the ventricular free wall 5, and onto which the supporting brackets 13 attach. The arms 17 of the device are adjustable in width and length and direction from [that] hinge point of the center part. They are inclined as a wide v -shaped embrace around the heart to avoid circumferential pressure on the coronary vessels. These arms 17 may be constructed from a flexible material in semi-rigid segments that are assembled to avoid pressure on the coronary circulation or the heart.

In another embodiment, the center part 15 alone may be affixed on the diaphragm or on the sternum.

Figure 4A:
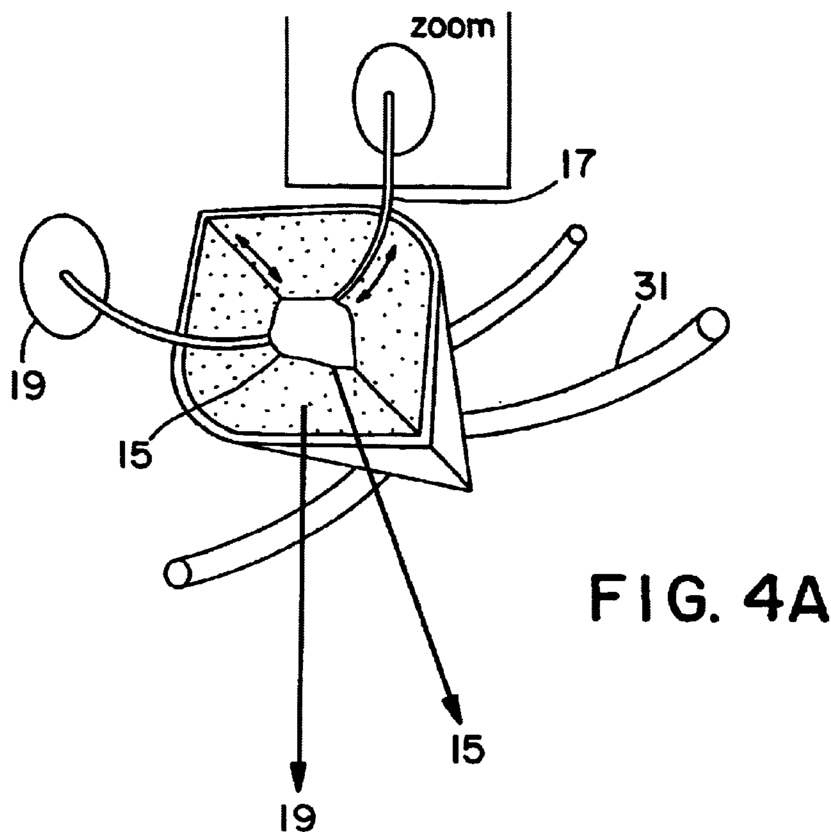
FIG. 4 shows components of the device with a wire mesh body.

In the embodiment shown in FIG. 4*a,* the center point 15 of the device would provide a wider mount for the arms. This center point 15 may be made of a wire mesh to avoid pressure, and also to provide a wider base on which the angulations and arm height and geometry could be more widely negotiated around the heart. In this embodiment, the hinge point of the arms 17 could be made to slide in any direction and, once adjusted, fastened onto the wire mesh with bio-compatible clips. After adjustment, the arms 17 would interlock with each other and the base. The interlocking arms 17 of such a device can function simultaneously or independently.

In another preferred embodiment, the pressure heads function dynamically, gated to respond by applying appropriate pressure at a certain target point on the heart, and at a specific time triggered point from the patients' cardiac cycle. The pressure heads could be operated mechanically or electrically with surgical rechargeable electrical batteries. The pressure head could also be operated by ultrasonic vibration build-up.

Figure 4B:
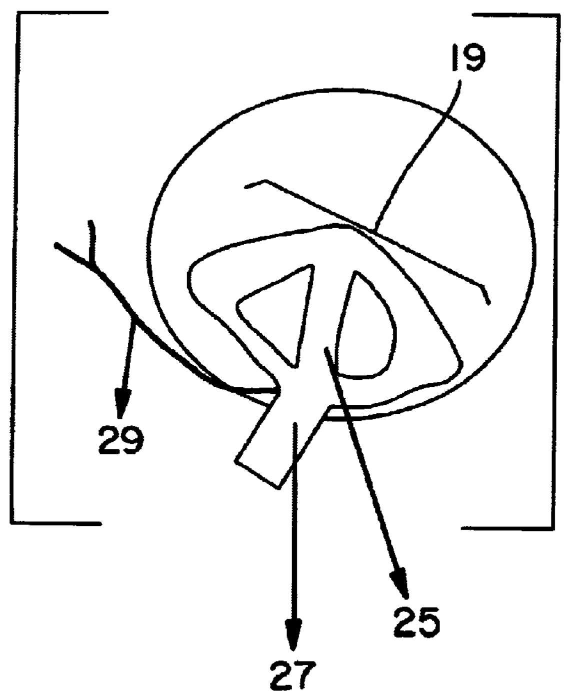

In another preferred embodiment as shown in FIG. 4*b,* a spring mechanism 25 is utilized for inducing pressure wherein housing and mounting of that spring 25 in a v-shape (towards the heart) or u-shaped or cap-like pressure head 19 will provide an axial compressing force that would correct the tethering geometry, thus providing inward displacement without distortion. Such a mechanism will provide a directed engagement on the desired target area of the heart. An amplifying diaphragm 27 can exaggerate those lever movements onto the spring 25. The pressure head 19 could be operated by mechanical expansion of the spring 25 modulated by a lever mechanism 29 that is sensed though diastolic expansion of the neighboring segment of the heart 1. In this model, a disc could be placed with a predetermined breaking point: a hinged release mechanism that pulls the spring off the pressure head. When this breaking pressure is no longer in effect, a biasing mechanism could be set to return the spring to its height and tension.

In another embodiment, where the pressure head is supported under a specific cup mechanism, a change of configuration the pressure head supports will release the pressure. Reciprocating the action will rebuild pressure through an ejector head, releasing the pressure build-up below.

There are examples of the different types of pressure heads that could be used. Pressurized fluid, as in a balloon valve or fluid filled bladder, with a pressure regulator timed to respond to the relaxation of the heart. Such timing would be triggered at the inner surface of the pressure head or at a side point by a pressure sensor mechanism. The pressure will be adjusted to the desired clinical effect. This could be programmed so as to have a proportionate sensing mechanism whereby smaller movements could result in a larger shift, or vice versa In another embodiment, the pressure head could be held at fixed pressure.

In another embodiment, the pressure delivered will be fixed by (a) a fluid filled bladder that is applied on the heart; or (b) a flexible bar with a depressed part that sits against the target point, and leveled parts of the arm extending on the heart.

In another embodiment, the following valve types to control pressure could be used on the pressure heads: (a) a diaphragm valve to control pressure; (b) any modification of a stop valve, or a popup assembly; (c) a ball valve; (d) a damper valve utilized at the interface of pressure head with the shaft, and (e) a diverter valve with a rod.

In another embodiment, a lever mechanism deflects a diaphragm controlling fluid level and valve timing and trigger technique is applied.

In another embodiment, pneumatic control with a pressure chamber could be utilized to exert the pressure needed.

In another embodiment, negative pressure could be applied by the similar to the above pressure control mechanisms. This will help relax a stiff ventricle.

In another embodiment, the pressure heads could also induce a negative pressure, and the positive force and surface upon which it acts could be adjusted and altered.

Figure 5:
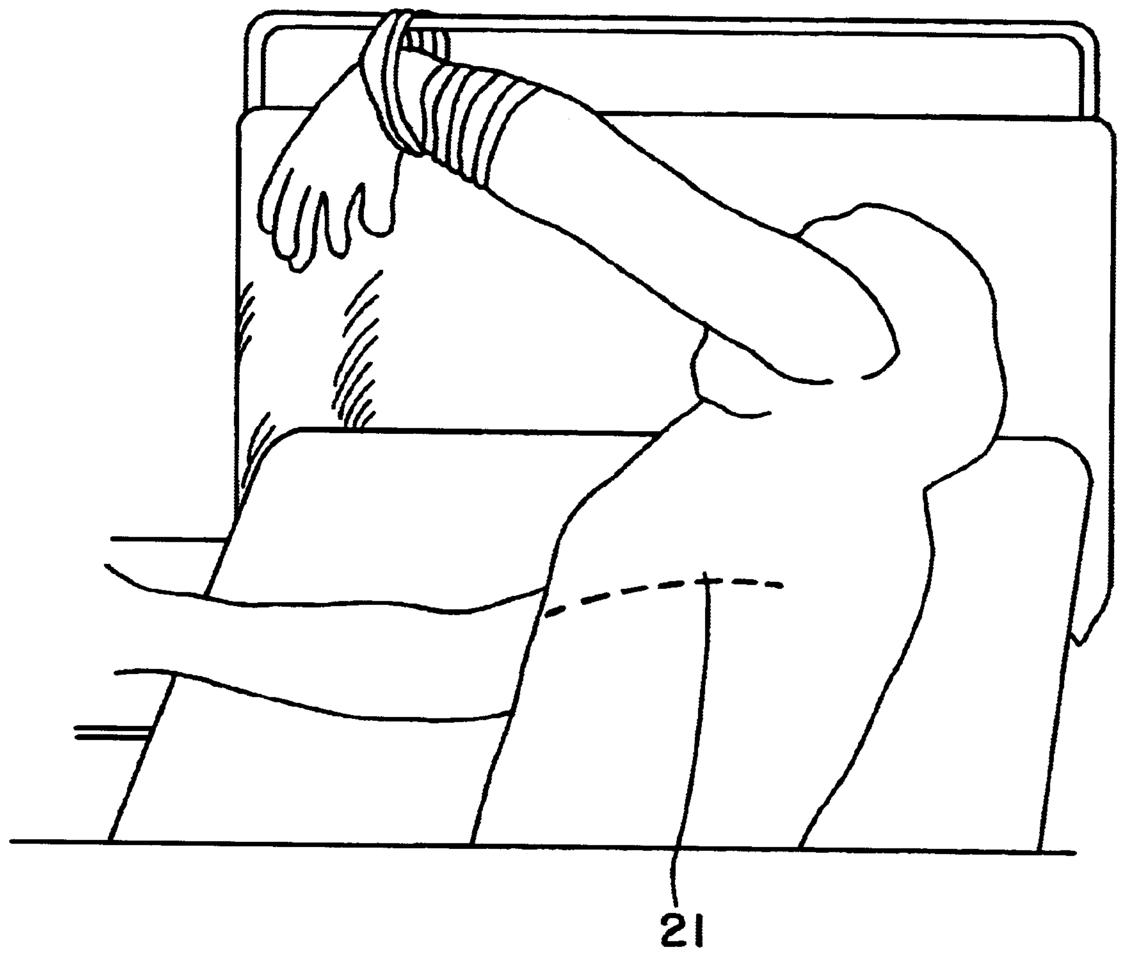
FIG. 5 shows an incision approach.

This device can be positioned without opening the heart, and without cardiopulmonary bypass. As shown in FIG. 5, an inframammary incision 21 is made overlying the fifth intercostal space, via a left thoracotomy, via a minimally invasive incision.

In another embodiment, the following access techniques could be used: (a) Thoracoscopy; (b) Minimally invasive lower sternotomy, and (c) Transdiaphragmatic approach. The incision is deepened, and the fibers of the pectoralis muscle are reached and dissected. The perichondrium of the fifth intercostal cartilage is incised and the perichondrial flaps are elevated. The fifth sixth, and seventh ribs, sternum or diaphragm or any part of the chest cavity or rib cage could be used, if needed for the attachments.

In another embodiment, any part of the bony cage, from the sternum, xiphoid or any rib, could be used as an anchor point for the supporting legs of the device, depending on individual patient cardiac geometry as depicted from echocardiographic scans and chest X-rays.

In another embodiment, the device could be fixed to the diaphragm.

Figure 6:
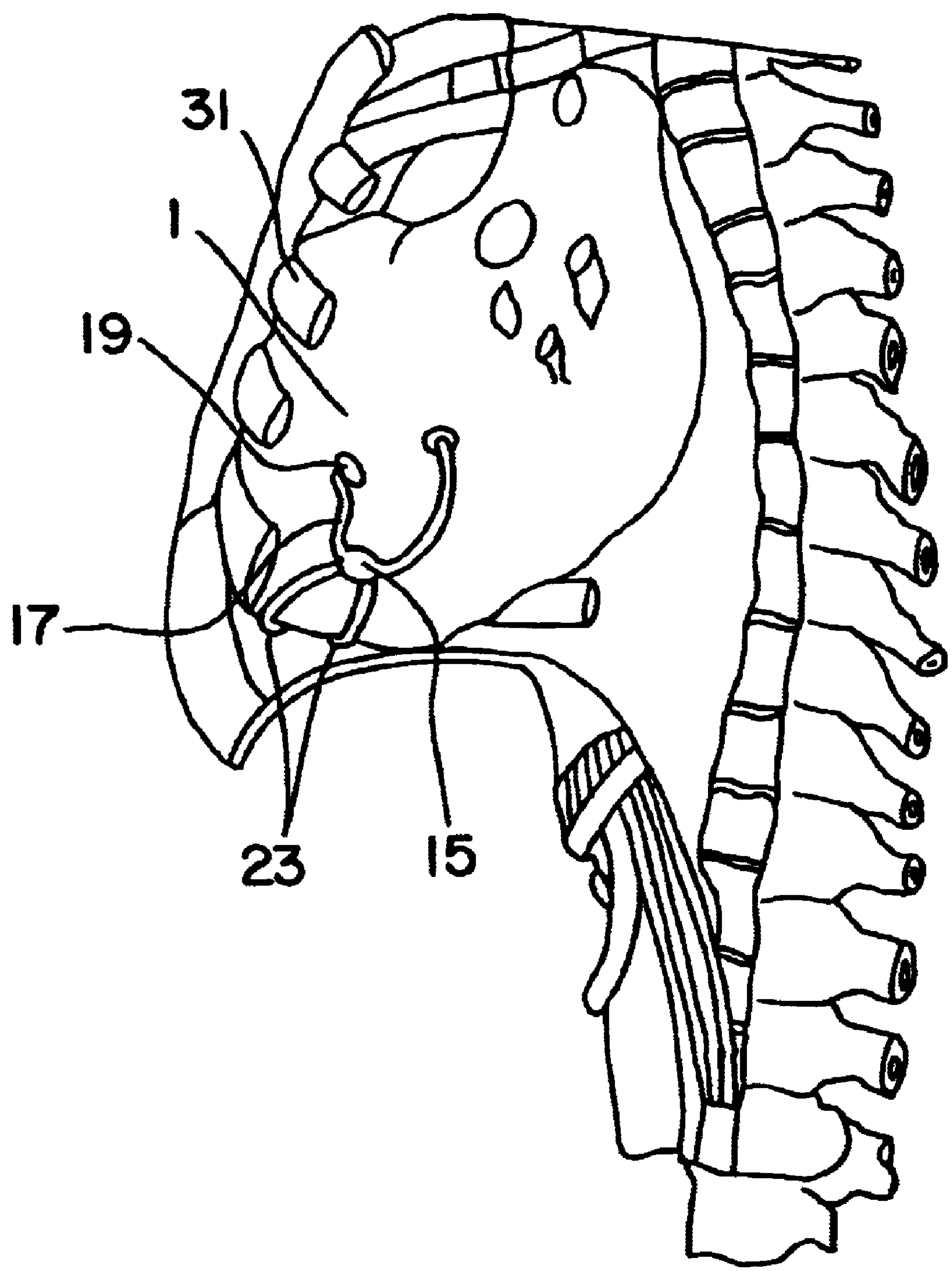
FIG. 6 shows orientation from ribs, around the heart and diaphragm

In a further embodiment shown in FIG. 6, the device is anchored to the rib cage, inside the ribs, following the rib curvature or hooking round the ribs 31. The attachment provides a solid anchor force to the device, and could be attached at two or more points at different angles and aspects of the rib cage. The attachment will be fastened to the rib cage by screws, clips, or other surgical stapling technique. The device has angulations directed toward the heart 1 and these angulations tightened appropriately relative to each other and to the heart. The device will be adaptable in depth and curvature. The supporting legs 13 of the device carry it like legs of a table inclined to suit the anatomical curvature of the patient's heart and extend to such length and curve so as to fit the device and slide it on the posteroinferior and lateral aspect of the heart 1. The center point 15 is the fulcrum point at which the legs 13 and the arms 17 of the device meet, and from which the arms 17 will be adjusted to the desired width and orientation, and then secured on the center point 15. The center point 15 fulcrum will be positioned in the space behind the posterolateral inferior aspect of the heart, halfway between the papillary muscles, at a position between the pericardial cavity and the pleural cavity on the left side. The arms 17 will then be extended, rotated, and mobilized in different directions to address the clinically relevant point of impact, i.e., the papillary muscles or relevant ventricular strain point. The impact and force adjusted will be done live, guided by hemodynamic monitoring of pressure changes, and cardiac output changes and also by direct intraoperative imaging of the disappearing mitral regurgitation.

In another embodiment, such strain points will be identified from intracardiac pressure measurements integrated on the dimensional echocardiographic-based dynamic finite element analysis modeling.

Figure 7:
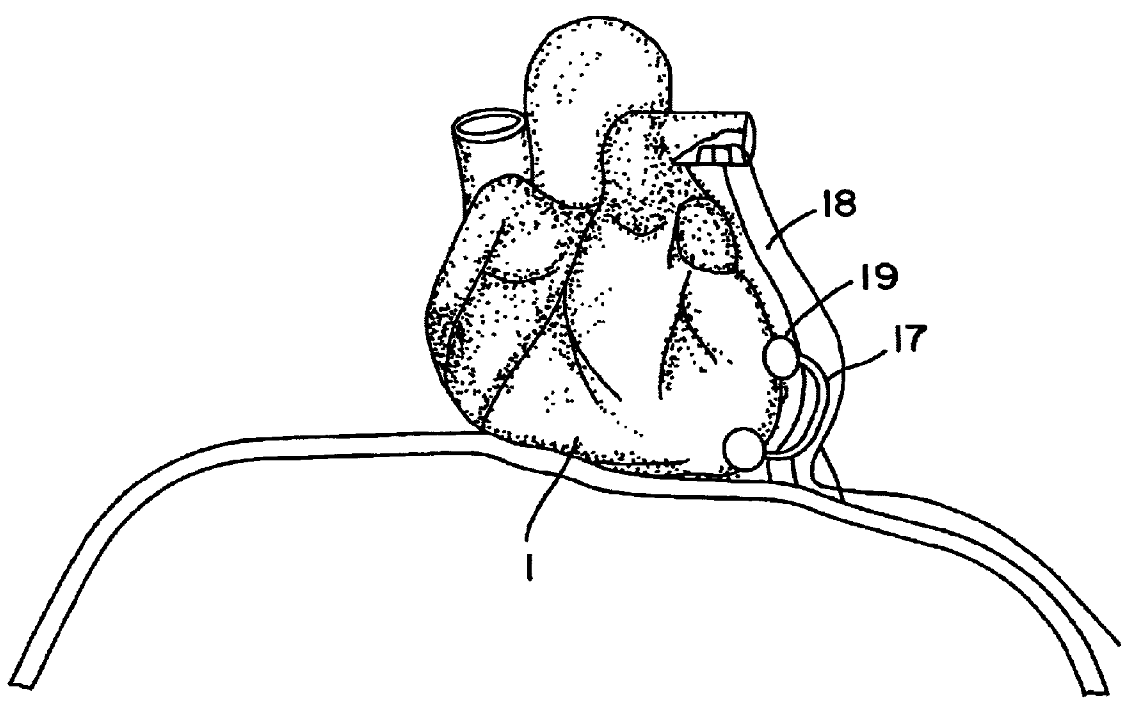
FIG. 7 shows the position of the device in the chest.

Looking now at the embodiment of FIG. 7, the present invention is shown wherein the center part 15 is free floating in the pleuropericordial space without supporting means 13, but with arms 17 and pressure heads 19 affixed to the heart.

Figure 8:
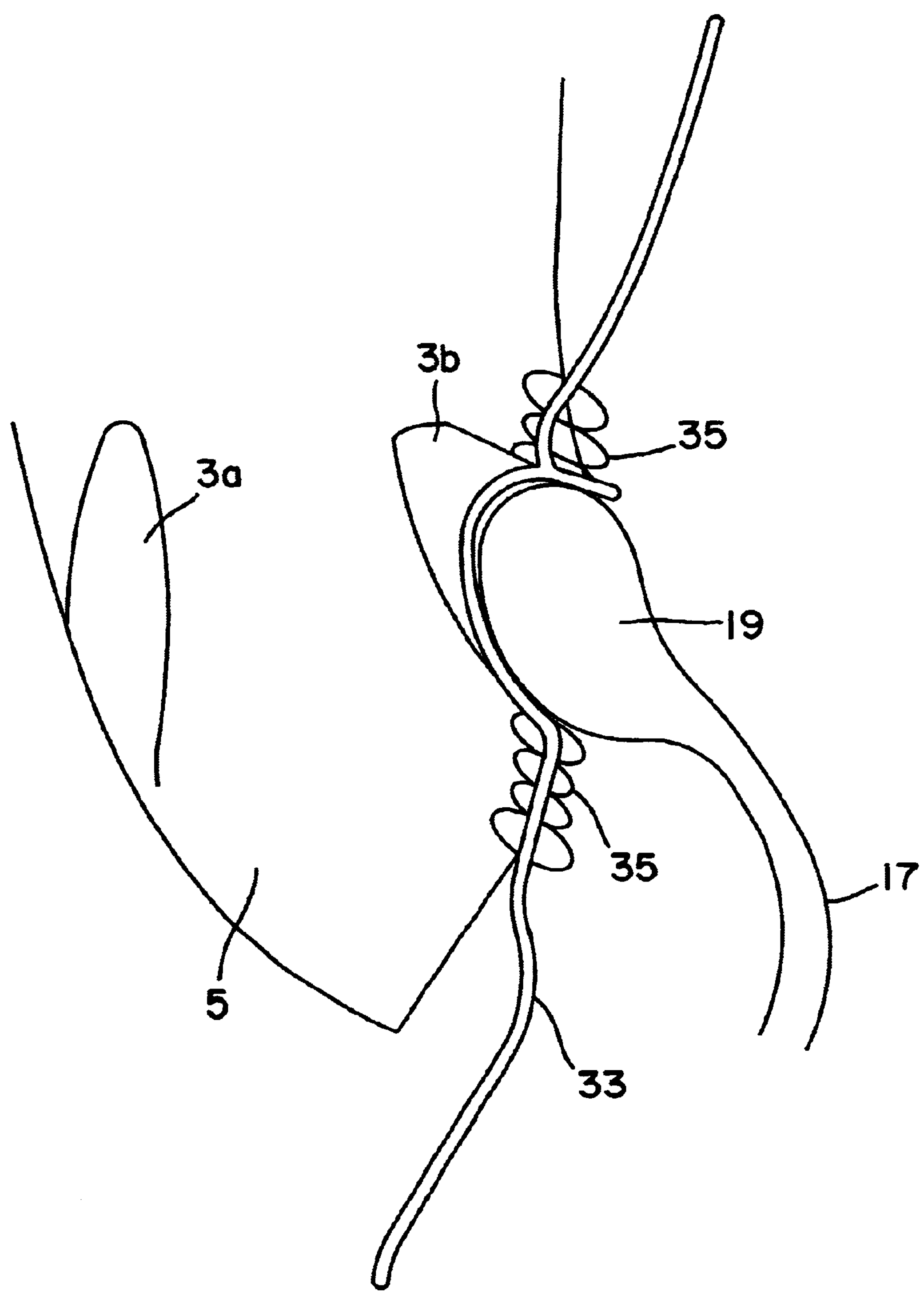
FIG. 8 shows attachment of the device to the heart.

In another embodiment as shown in FIG. 8 the device could be applied around the heart 1 [FIG. 8 (4)] from different perspectives encompassing dilations, restrictions, and geometrical changes from all angles. The pericardium overlying the desired pressure target point is incised around the pressure head 19. The outside surface of the pericardium 33 towards the pleura is fixed to the pressure head of the device. The inside surface of the pericardium 33 at this localized part, and around the rim of the device is adhered to the myocardium. A very localized adhesion of pericardium 33 to myocardium will provide a vascularized support needed for the head of the device, and will keep it abutting the desired target point as a button hole for a button. That localized portion of the pericardium 33 is later adhered to the myocardium by surgical stitches 35 as shown, chemical adherence, or surgical stapling material, thus stabilizing the pressure head 19 against the intended target point on the heart 1. The device is then entrapped into this target area. This could be oriented so as not to interfere with the coronary flow. The surface area of overlap of the pressure head 19 could be altered to cover a smaller or more extensive area of the heart. This eliminates the need for opening the heart, and as a specific advantage, utilizes the vascularity of the pericardium to ensure adequate blood supply. The surrounding pressure head is stitched to the pericardium 33 or fixed in other embodiments by glue, staples, or other means of adherence. The pericardium 33 is tightly secured around the pressure head 19 as it emerges inside the pericardial cavity and abuts the surface of the heart 1. The force of this spring or pressure will be adjusted accordingly in each embodiment. It will be optimized by the actual echocardiographic and hemodynamric evidence of the restoration of the valvular or ventricular integrity. The applied pressure could also be designed to provide a negative suction force. The incision is then closed.

In another embodiment, the device could be assembled so as to be introduced by small thoracoscopic techniques and robotic arms.

Although the invention has been described with respect to various embodiments, it should be realized this invention is also capable of a wide variety of further and other embodiments within the spirit and scope of the appended claims.

What is claimed is:

1. An adjustable periventricular device for a patient, comprising:

supporting brackets attachable to different surfaces, curvatures, and geometric orientations of one or more portions of the patient in the region of the heart;

swiveling adjustable arched arms being adjustable in width and length to different surfaces, curvatures, and geometric orientations, having a hinge point;

a center part on which said swiveling adjustable arched arms rest, said center part fixable to the patient's diaphragm;

pressure heads affixable to different surfaces, curvatures, and geometric orientations of a patient's heart to provide corrective forces thereto, said pressure heads being held by said swiveling adjustable arched arms at their end, said pressure heads being interchangeable to wider size; and a fixing cuff around said pressure heads to stabilize said heads when affixed to a heart.

2. An adjustable periventricular device as defined in claim 1, wherein said center part is a simple base fulcrum point from which said swiveling adjustable arched arms extended to surround a heart and onto which said supporting brackets meet.

3. An adjustable periventricular device as defined in claim 1, wherein said swiveling adjustable arched arms comprising semirigid segments assembled to avoid pressure on the patent's coronary and heart circulation when affixed to a heart.

4. An adjustable periventricular device as defined in claim 1, wherein said center part is a wire mesh.

5. An adjustable periventricular device as defined in claim 1, wherein said hinge point of said swiveling adjustable arched arms are made to slide in any direction and being used together or independently.

6. An adjustable periventricular device as defined in claim 1, wherein said pressure heads being in function dynamically gated to respond by applying an appropriate pressure at a certain target point on a heart and at a specific time triggered point, said pressure heads being operated mechanically, electrically with surgical rechargeable electrical batteries, or ultrasonic vibration.

7. An adjustable periventricular device as defined in claim 1, wherein said pressure heads being operated by expansion a spring modulated by a lever mechanism that is sensed though diastolic expansion of the neighboring segment of the heart.

8. An adjustable periventricular device as defined in claim 1, wherein said pressure heads being supported under a specific cup mechanism.

9. An adjustable periventricular device as defined in claim 1, wherein said pressure heads being used as pressurized fluid with a pressure regulator timed to respond to the relaxation of the heart.

10. An adjustable periventricular device as defined in claim 1, wherein valve types being used to control pressure on said pressure heads, said valve types being selected from a group consisting of a diaphragm valve, a stop valve, a popup assembly valve, a ball valve, a damper valve and a diverter valve with a rod.

11. An adjustable periventricular device as defined in claim 1, wherein pressures on said pressure heads being controlled by pneumatic control with a pressure chamber.

12. An adjustable periventricular device as defined in claim 1, whereas pressures on said pressure heads being fixed by a fluid filled bladder that is applied on a heart.

13. An adjustable periventricular device as defined in claim 1, wherein pressures on said pressure heads being fixed by a flexible bar that has a depressed part sitting against a target point and a leveled part of said swiveling adjustable arched arms extend on a heart.

14. An adjustable periventricular device as defined in claim 1, wherein negative pressure can be applied to help relax a stiff ventricle.

15. An adjustable periventricular device as defined in claim 1, wherein said device is affixed to a heart by access techniques selected from the groups consisting of thoracoscopy, minimally invasive lower sternotomy, and transdiaphragmatic approach, said swiveling adjustable arched arms being extended, rotated and mobilized in different directions to address the clinically relevant point of impact.

16. An adjustable periventricular device comprising:

a center element having a hinge point;

a pair of swiveling arms extending upward from the hinge point of the center element and having pressure heads at each arm on the end opposite the hinge point, such pressure heads being affixable to a heart and providing an axial compressing force when affixed thereto; and a support means to affix the center element to a portion of the chest cavity, including structures therein.

17. An adjustable periventricular device comprising:

a center element having a hinge point;

a support means to affix the center element to a portion of a chest cavity; and a pair of arms extending upward from the hinge point of the center element and having pressure heads at each arm on the end opposite the hinge point, such pressure heads being affixable to a heart and providing an axial compressing force when affixed thereto.

* * * * *